United States Patent [19]

Fields, Jr. et al.

[11] Patent Number: 4,889,906

[45] Date of Patent: Dec. 26, 1989

[54] AMINE SALTS OF 1,4,2-OXAZAPHOSPHOLIDINE-4-ACETIC ACID, 2-ALKOXY-2-OXIDES

[75] Inventors: Donald L. Fields, Jr., Manchester; Raymond C. Grabiak, Maryland Heights, both of Mo.

[73] Assignee: Monsanto Company, St. Louis, Mo.

[21] Appl. No.: 276,009

[22] Filed: Nov. 25, 1988

[51] Int. Cl.$^4$ .............................................. C07F 9/15
[52] U.S. Cl. .................................................... 558/81
[58] Field of Search ......................................... 558/81

[56] References Cited

U.S. PATENT DOCUMENTS

| | | | |
|---|---|---|---|
| 3,172,903 | 3/1965 | Reetz et al. | 558/81 |
| 3,799,758 | 3/1974 | Franz | 71/86 |
| 4,062,669 | 12/1977 | Franz | 71/86 |
| 4,190,651 | 2/1980 | Eto et al. | 558/81 |
| 4,387,060 | 6/1983 | Hoffmann et al. | 558/81 |
| 4,486,359 | 12/1984 | Brendel et al. | 260/502.5 F |
| 4,601,744 | 7/1986 | Sikorski et al. | 71/86 |

FOREIGN PATENT DOCUMENTS 1958125  5/1971  Fed. Rep. of Germany ........ 558/81

*Primary Examiner*—Anton H. Sutto
*Attorney, Agent, or Firm*—Frank D. Shearin

[57] ABSTRACT

The compounds 1,4,2-oxazapholidine-4-acetic acid, 2-alkoxy-2-oxides and their trialkylamine salts represented by the formula

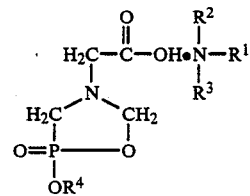

wherein $R^1$, $R^2$, $R^3$ and $R^4$ are individually selected from the group consisting of alkyl having from one to about four carbon atoms are useful as post emergent, selective herbicides and plant growth regulators.

6 Claims, No Drawings

AMINE SALTS OF 1,4,2-OXAZAPHOSPHOLIDINE-4-ACETIC ACID, 2-ALKOXY-2-OXIDES

BACKGROUND OF THE INVENTION

This invention relates to novel organophosphorus amines, and more particularly relates to novel amine salts of 1, 4, 2-oxazaphospholidine-4-acetic acid, 2-alkoxy-2-oxides and the use of such compounds as a herbicide and plant growth regulator.

There are numerous references in the prior art that disclose various organophosphorus compounds. For example, U.S. Pat. No. 3,172,903 discloses that certain 1,3,2-oxazaphospholidine and 1,3,2-oxazaphospholidine phosphorus ester compounds are useful as fungicides. U.S. Pat. No. 4,190,651 discloses that certain 4-substituted 1,3,2-oxazaphospholidine derivatives are useful as insecticides. U.S. Pat. No. 4,387,060 discloses a synergistic insecticidal composition containing 2-(thi)oxo-1,3,2-oxazaphospholane of defined formula.

Other organophosphorus compounds are known to have biological activity on plants. For example, U.S. Pat. No. 3,799,758 to Franz discloses that N-phosphonomethylglycine and its salts are useful as a broad spectrum herbicide and has a phytotoxic effect on most terrestrial and aquatic plants. U.S. Pat. No. 4,486,359 to Brendel et al discloses that N-phosphonomethylglycine can be prepared from glycine and paraformaldehyde to obtain an intermediate which is reacted with a dialkylphosphite to obtain an ester of the desired compound, which is then hydrolized. U.S. Pat. No. 4,062,669 to Franz disloses that N-organo-N-phosphonomethylglycine-N-oxides and derivatives thereof are useful in herbicidal compositions and methods, and that the compounds and the compositions containing them are useful as phytotoxicants and as plant growth regulants. U.S. Pat. No. 4,601,744 to Sikorski et al discloses that ester of N,N'-methylene-bis-[N-[-(diaryloxyphosphinyl)methyl]glycine]are useful as herbicides.

Despite these and other references in the prior art, there is now provided a novel 1, 4, 2-oxazaphospholidine compounds that have selective phytotoxic activity, i.e. they have a herbicidal effect upon certain plant species but do not have a phytotoxic effect on other plant species, and have a plant growth regulant activity, i.e. stunt or retard the growth rate of certain plants without phytotoxicity.

SUMMARY OF THE INVENTION

These and other advantages are achieved by compounds represented by the formula:

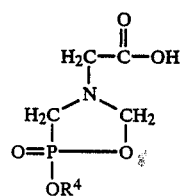

wherein $OR^4$ is an alkyl group having from 1 to about 4 carbon atoms. A particularly preferred embodiment of this invention is the tertiary amine salt of the 1,4,2-oxazaphospholidine-4-acetic acid, 2-alkoxy-2-oxide represented by the above formula, and which amine salt can be represented by the following structural formula:

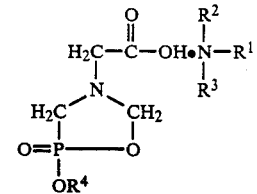

wherein $R^1$, $R^2$ and $R^3$ are individually selected from alkyl groups having from one to about four carbon atoms.

DETAILED DESCRIPTION OF THE INVENTION

Although applicants do not wish to be bound by any particular theory, it is believed that the 1,4,2-oxazaphospholidine-4-acetic acid, 2-alkoxy-2oxide compounds of the present invention, represented by the above formulas, enter the plant and form an anion as represented by the following structural formula:

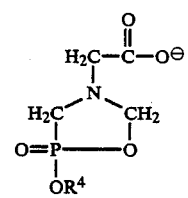

wherein $R^4$ is as defined above. It is believed that this anion is responsible for the selective herbicidal activity and plant growth regulant properties exhibited by the novel compounds of the present invention.

The compounds of the present invention can be prepared from the known reactants, glycine, formaldehyde, trialkylamine and dialkyl phosphite, i.e. dimethyl phosphite, diethyl phosphite, methylethylphosphite, diisopropylphosphite, dibutylphosphite and the like. Mixed esters and branched derivatives can also be used. Dimethylphosphite and diethylphosphite are preferred.

Another reactant is a trialkyl amine wherein the alkyl group contains from one to about four carbon atoms. Examples of such trialkyl amines include trimethylamine, triethylamine, tributylamine, triisopropylamine, tri-t-butylamine, and mixtures such as diethylmethylamine, dibutylethylamine, and the like. Trimethylamine and triethylamine are preferred, since they are readily available.

To prepare the compounds of the present invention, formaldehyde and a trialkylamine are heated to solution in an anhydrous solvent, such as methanol, ethanol, propanol, isopropynol, t-bitynol, butanol, and the like. Methanol is preferred. Thereafter, glycine is added with heat and stirring, and then the dialkyl phosphite is added to the solution and heated. There is then provided the trialkylamine salt of 1,4,2-oxazaphospholidine-4-acetic acid, 2-alkoxy-2-oxide.

The acid can be prepared by passing the solution of the amine salt in anhydrous alcohol through a weakly acidic cation exchange resin to remove the trialkylamine and provide the 1,4,2-oxazaphospholidine-4-acetic acid, 2-alkoxy-2-oxides.

The mole ratio of the reactants influences the yield of the desired product. In general, most of the reactants are in a mole ratio of about 1:1, based on glycine, except that formaldehyde should be used in excess, preferably 2:1 or 3:1 or higher.

The temperature of the dialkyl phosphite addition can vary from about room temperature to about 75° C. Satisfactory results have been achieved at temperatures between about 25° C. and about 60° C.

The products of the above reaction are useful as selective post emergent herbicides by providing phytotoxic activity on cocklebur, morningglory, barnyardgrass, yellow nutsedge and quackgrass. The compounds are also useful to control the growth rate on desirable grasses, such as fescue.

Typically the biologically active compounds of this invention are provided in the form of concentrates which require dilution prior to application to plants. The usual means for diluting the concentrate, whether either liquid or solid, comprising adjuvants, inert materials and the like, are known to those skilled in the art. The compositions containing concentrates which require dilution prior to application to the plants contain from about 5 to 95 parts by weight of at least one compound of the present invention, and from 5 to 95 parts by weight of an adjuvant in liquid or solid form, for example, from about 0.25 to 25 parts by weight of a wetting agent, from about 0.25 to 25 parts by weight of a dispersant, and from about 4.5 to about 94.5 parts by weight of an inert liquid extender, such as water, acetone, tetrahydrofuran and the like. The composition can also contain other materials as will occur to those skilled in the art in view of this disclosure.

When operating in accordance with the teachings of the present invention, effective amounts of the compounds or compositions of the present invention are applied to the plants or are incorporated into aquatic media in any conventional fashion. The compositions can also be applied from airplanes as a dust or spray by means known to those skilled in the art.

The application of an effective amount of the compound or composition of the present invention to the plant is essential and critical for the practice of the present invention. The exact amount of the active ingredient to be employed is dependent upon the response desired in the plant, as well as such other factors such as the plant species, stage of development, the amount of rainfall, as well as the specific compound employed. It is believed that one skilled in the art can readily determine from the teachings of this specification, including the examples, the approximate application rate.

The invention is further illustrated by, but not limited to, the following examples, where all percentages are by weight unless otherwise indicated.

EXAMPLE 1

Preparation of triethylamine salt of 1,4,2-oxazaphospholidine-4-acetic acid, 2-methoxy-2-oxide.

Triethylamine (5.05 g, 0.05 mol) and paraformaldehyde (3.0 g, 0.10 mol) were heated to solution (55° C.) in methanol (50 ml). Glycine (3.75 g, 0.05 mol) was added in one portion and the mixture was heated at reflux for one hour. The solution was cooled to room temperature, and dimethyl phosphite (5.5 g, 0.05 mol) was added in one portion. The solution was heated at reflux for 40 minutes upon which time the $^{31}P$ NMR spectra showed the absence of dimethyl phosphite. The methanol in the reaction mixture was removed on a rotary evaporator at 35° C. and reduced pressure (25 mm, $33.35 \times 10^2 N/m^2$) to yield 15.4 g of a light yellow oil, which was confirmed to be the desired compound by $^1H$ NMR, $^{13}C$ NMR and $^{31}P$ NMR spectral analyses.

EXAMPLE 2

Preparation of 1, 4, 2-oxazaphospholidine-4-acetic acid, 2-alkoxy-2-oxide.

The procedure of Example 1 was repeated to obtain the light yellow oil, which was then dissolved in methanol (50 ml) and the solution was passed through a 30 cm long column of Amberlite ™ CG-50 slightly acetic cation exchange resin available from Rohm & Haas Company of West Philadelphia, Pa. Analysis by $^1H$ NMR, $^{13}C$ NMR and $^{31}P$ NMR confirmed the presence of the desired compound.

EXAMPLE 3

Post-Emergent Herbicide Activity.

The post-emergent herbicidal activity of the compound of Example 1 was demonstrated by greenhouse testing. Top soil was placed in pans having holes in the bottom and compacted to a depth of 0.95 to 1.27 cm from the top of the pan. A predetermined number of seeds of each of several plant species or vegetative propagules for perennial plant species were placed on the soil and pressed into the soil surface. The seeds or propagules were covered with soil and leveled. The pans were then placed on a bench in the greenhouse and watered as needed for germination and growth. After the plants reached the desired age (2 to 3 weeks) each pan, except the control pans, was removed to a spraying chamber and sprayed by means of an atomizer. In the spray solution, an emulsifying agent was added to give a spray solution which contains about 0.4% by volume of the emulsifier. The spray solution contained a sufficient amount of the compound of Example 1 to give an application rate of the active ingredient of 2.8 g/m² (25 lbs. per acre) and 5.6 g/mz (50 lbs. per acre), while applying a total amount of solution equivalent to 187 ml/m² (200 gal per acre). The pans were returned to the greenhouse and watered as before, and the injury to the plants as compared to those in control pans was observed after 14 days after spraying, and again, 27 days after spraying.

After 27 days the post emergent herbicide activity was observed at a rate of application of 5.6 g/m². The data are shown in Table I.

TABLE I

| Plant | Plant Response* After | |
| Species | 14 Days | 27 Days |
| --- | --- | --- |
| Canada Thistle | 0 | 0 |
| Cocklebur | 1 | 1 |
| Velvetleaf | 0 | 0 |
| Morningglory | 1 | 1 |
| Common Lambsquarters | 0 | 0 |
| Pennsylvania Smartweed | 0 | 0 |
| Yellow Nutsedge | 0 | 1 |
| Quackgrass | 0 | 1 |
| Rhizone Johnsongrass | 0 | 0 |
| Downy Brome | 0 | 0 |
| Barnyardgrass | 1 | 1 |
| *Plant Response | Index | |
| 0–24% inhibition | 0 | |
| 25–49% inhibition | 1 | |
| 50–74% inhibition | 2 | |
| 75–99% inhibition | 3 | |

TABLE I-continued

| Plant Species | Plant Response* After | |
|---|---|---|
| | 14 Days | 27 Days |
| 100% inhibition | | 4 |

EXAMPLE 4

Plant Growth Regulating Activity.

The plant growth regulating activity of the compound of Example 1 was demonstrated by greenhouse testing. Established stands of fescue (Kentucky bluegrass No. 31) in pots having an area of about 100 cm (16 square inches) were trimmed to a uniform height. Duplicate pots were removed to a spraying chamber and sprayed by means of an atomizer as in Example 3. The application rate of the active ingredient was 0.56 g/m$^2$ (5 lbs. per acre) while applying a total amount of solution equivalent to 187 ml/m$^2$ (200 gal/acre). The pots were returned to the greenhouse and watered with the controls on a daily basis. After two weeks, the height of the grass was measured. The control pots grew an average of 199.58 mm over the two-week period, and the pots treated with the compound of Example 1 grew 80 and 90 mm, showing that the treated fescue had an average growth rate of 43% of the controls. The grass did not show any discoloration or other sign of phytotoxicity.

EXAMPLE 5

Preparation of Triisopropylamine Salt of 1, 4, 2-Oxazaphospholidine-4-Acetic Acid, 2-Methoxy-2-Oxide.

The procedure of Example 1 is repeated except that 0.05 mol of triisopropylamine is substituted for the triethylamine used in Example 1. Analysis by spectral data indicates the presence of the desired triisopropylamine salt of 1, 4, 2-oxazaphospholidine-4-acetic acid, 2-methoxy-2-oxide.

EXAMPLE 6

Biological Activity.

The compound of Example 2 and the compound of Example 5 is tested in greenhouse tests according to the procedure of Examples 3 and 4. Satisfactory results are achieved.

Although the invention has been described in terms of specified embodiments, which are set forth in considerable detail, it should be understood that this is by way of illustration only, and that alternative embodiments and operating techniques will become apparent to those skilled in the art in view of the disclosure. For example, other salts of the 1,4,2-oxazaphospholidine-4-acetic acid, 2-alkoxy-2-oxide of the present invention, such as the sulfate, chloride, bromide, and the like can be substituted for the trialkylamine, provided they do not cause decomposition of the acid. Accordingly, modifications can be made without departing from the spirit of the described invention.

WHAT IS CLAIMED IS:

1. A compound represented by the formula:

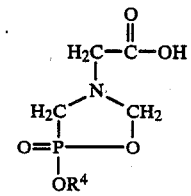

wherein R$^4$ is an alkyl having from one to about four carbon atoms.

2. A compound of claim 1 wherein R$^4$ is methyl.
3. A compound of claim 1 wherein R$^4$ is ethyl.
4. A compound of claim 1 as the trialkylamine salt which is represented by the formula:

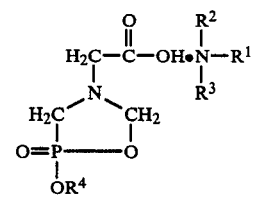

wherein R$^1$, R$^2$ and R$^3$ are individually selected from the group consisting of alkyl having from one to about four carbon atoms.

5. A compound of claim 4 wherein R$^1$, R$^2$, R$^3$ and R$^4$ are independently selected from methyl or ethyl.
6. A compound of claim 4 wherein R$^1$, R$^2$ and R$^3$ are ethyl and R$^4$ is methyl.

* * * * *